(12) United States Patent
Weber et al.

(10) Patent No.: US 12,290,441 B2
(45) Date of Patent: *May 6, 2025

(54) MULTIPLE PUMP SYSTEM FOR INFLATABLE PENILE PROSTHESIS

(71) Applicant: Boston Scientific Scimed, Inc., Maple Grove, MN (US)

(72) Inventors: Jan Weber, Maastricht (NL); Noel Smith, County Kilkenny (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 739 days.

This patent is subject to a terminal disclaimer.

(21) Appl. No.: 17/447,112

(22) Filed: Sep. 8, 2021

(65) Prior Publication Data

US 2021/0393406 A1  Dec. 23, 2021

Related U.S. Application Data

(63) Continuation of application No. 16/409,134, filed on May 10, 2019, now Pat. No. 11,135,063.

(60) Provisional application No. 62/671,583, filed on May 15, 2018.

(51) Int. Cl.
  *A61F 2/26* (2006.01)
(52) U.S. Cl.
  CPC ........................ *A61F 2/26* (2013.01)
(58) Field of Classification Search
  CPC ....................................................... A61F 2/26
  See application file for complete search history.

(56) References Cited

U.S. PATENT DOCUMENTS

| 5,171,272 A | 12/1992 | Levius |
| 11,135,063 B2 * | 10/2021 | Weber ........................ A61F 2/26 |
| 2014/0094727 A1 | 4/2014 | Deshpande et al. |

FOREIGN PATENT DOCUMENTS

| CN | 101125109 A | 2/2008 |
| CN | 102429744 A | 5/2012 |
| WO | 9204879 A1 | 4/1992 |
| WO | 2015093681 A1 | 6/2015 |
| WO | 2015200784 A3 | 12/2015 |

OTHER PUBLICATIONS

International Search Report and Written Opinion for Application No. PCT/US2019/031999, mailed on Sep. 25, 2019, 16 pages.
"Micro Dosing", Fraunhofer EMFT, retrieved from https://www.emft.fraunhofer.de/en/competences/micro-dosing.html, May 31, 2021, 4 pages.

(Continued)

*Primary Examiner* — Samuel G Gilbert
(74) *Attorney, Agent, or Firm* — Brake Hughes Bellermann LLP (57) ABSTRACT

According to an aspect, an inflatable penile prosthesis includes a fluid reservoir configured to hold fluid, an inflatable member, and a pump assembly configured to transfer the fluid from the fluid reservoir to the inflatable member during an inflation cycle. The pump assembly includes a first pump configured to inject the fluid into the inflatable member according to a first flow rate, and a second pump configured to inject fluid into the inflatable member according to a second flow rate, where the second flow rate is less than the first flow rate.

17 Claims, 8 Drawing Sheets

(56) References Cited

OTHER PUBLICATIONS

"Silicon Micro Diaphragm Pumps Portfolio", Fraunhofer EMFT, retrieved on Jun. 2, 2021 from https://www.emft.fraunhofer.de/content/dam/emft/en/documents/Infosheets/19_E_Micro_Diaphragm_pumps_portfolio_of_Fraunhofer_EMFT_public.pdf, 2 pages.
"The Smallest Micropump in the World", Fraunhofer EMFT, Press briefing, retrieved from https://www.emft.fraunhofer.de/en/mediacenter/press-briefings/2015-11-16_smallest-micropump.html, Nov. 16, 2015, 2 pages.
Lewis, et al., "Blood Pressure Within the Corpus Cavernosum Penis of the Bull", J. Reprod. Fert. 17, 1968, pp. 155-156.
Scovell, et al., "Longitudinal and Horizontal Load Testing of Inflatable Penile Implant Cylinders of Two Manufacturers: An Ex Vivo Demonstration of Inflated Rigidity", J Sex Med. 13(11), Nov. 2016, 14 pages.
Wu, et al., "MEMS Flow Sensors for Nano-Fluidic Applications", Sensors and Actuators A 89, 2001, pp. 152-158.
First Office Action for Chinese Application No. 201980029084.2 (with English Translation), mailed Jan. 18, 2023, 18 pages.

* cited by examiner

MULTIPLE PUMP SYSTEM FOR INFLATABLE PENILE PROSTHESIS

CROSS-REFERENCE TO RELATED APPLICATIONS

This application is a continuation of, and claims priority to, U.S. patent application Ser. No. 16/409,134, filed on May 10, 2019, entitled "MULTIPLE PUMP SYSTEM FOR INFLATABLE PENILE PROSTHESIS", which claims priority to U.S. Provisional Patent Application No. 62/671,583, filed on May 15, 2018, entitled "MULTIPLE PUMP SYSTEM FOR INFLATABLE PENILE PROSTHESIS", the disclosures of which are incorporated by reference herein in their entirety.

TECHNICAL FIELD

This disclosure relates generally to bodily implants and more specifically to bodily implants, such as penile prosthesis that includes a multiple pump system.

BACKGROUND

One treatment for male erectile dysfunction is the implantation of a penile prosthesis that mechanically erects the penis. Some existing penile prostheses include inflatable cylinders or members that can be inflated or deflated using a pump mechanism. The pump mechanism pulls fluid from a fluid reservoir and then transfers the fluid to the inflatable members. According to some existing designs of inflatable penile prostheses, the amount of time, energy and disparity from the occurrence of a normal human male erection for the patient to inflate a penile prosthesis (e.g., the number of pumps and time required to provide the desired penis rigidity) may be relatively high.

SUMMARY

According to an aspect, an inflatable penile prosthesis includes a fluid reservoir configured to hold fluid, an inflatable member, and a pump assembly configured to transfer the fluid from the fluid reservoir to the inflatable member during an inflation cycle. The pump assembly includes a first pump configured to inject the fluid into the inflatable member according to a first flow rate, and a second pump configured to inject fluid into the inflatable member according to a second flow rate, where the second flow rate is less than the first flow rate.

According to some aspects, the inflatable penile prosthesis may include one or more of the following features (or any combination thereof). The first pump may include a plurality of micro-pumps, and the second pump may include a plurality of micro-pumps. The first pump is configured to inject the fluid into the inflatable member up to a first maximum output pressure, and the second pump is configured to inject the fluid into the inflatable member up to a second maximum output pressure, where the second maximum output pressure is higher than the first maximum output pressure. The second pump may be disposed in parallel with the first pump. The pump assembly is configured to move between a parallel configuration in which the second pump is disposed in parallel with the first pump and a serial configuration in which the second pump is disposed in serial with the first pump. The inflatable penile prosthesis may include a controller configured to actuate a plurality of valves to move between the parallel configuration and the serial configuration. The controller may activate the first pump during a first phase of the inflation cycle, and may activate the second pump during a second phase of the inflation cycle. The controller may activate the second pump during the second phase of the inflation cycle in response to a pressure level in the inflatable member exceeding a threshold level. The fluid reservoir may include a flexible fluid container disposed within a cavity of the fluid reservoir. The flexible fluid container may enclose fluid at a higher pressure than the fluid contained in the fluid reservoir. At least one of the first pump or the second pump is configured to transfer the fluid in the fluid reservoir during a first phase of the inflation cycle, and the fluid contained in the flexible fluid container is transferred to the inflatable member during a second phase of the inflation cycle. The fluid contained in the flexible fluid container may be transferred to the inflatable member after the inflation cycle.

According to an aspect, an inflatable penile prosthesis includes a fluid reservoir configured to hold fluid, an inflatable member, and a pump assembly configured to transfer the fluid from the fluid reservoir to the inflatable member during an inflation cycle. The pump assembly includes a first pump configured to inject the fluid into the inflatable member, a second pump configured to inject fluid into the inflatable member, and a controller configured to activate the first pump during a first phase of the inflation cycle, and activate at least the second pump during a second phase of the inflation cycle.

According to some aspects, the inflatable penile prosthesis may include one or more of the following features (or any combination thereof). The first pump may include a plurality of micro-pumps disposed on a first substrate, and the second pump may include a plurality of micro-pumps disposed on a second substrate. A number of the plurality of micro-pumps disposed on the first substrate may be less than a number of the plurality of micro-pumps disposed on the second substrate. The first pump is configured to inject the fluid into the inflatable member according to a first flow rate up to a first maximum output pressure, and the second pump is configured to inject the fluid into the inflatable member according to a second flow rate up to a second maximum output pressure, where the first flow rate is higher than the second flow rate, and the second maximum output pressure is higher than the first maximum output pressure. The fluid reservoir may include a flexible fluid container disposed within a cavity of the fluid reservoir, and the flexible fluid container may enclose fluid at a higher pressure than the fluid contained in the fluid reservoir.

According to an aspect, a method of inflating an inflatable member of a penile prosthesis includes transferring, by a first pump of a pump assembly, fluid from a fluid reservoir to the inflatable member during a first phase of an inflation cycle, detecting, by a sensor, a pressure level in the inflatable member, activating, by a controller connected to the sensor, a second pump of the pump assembly in response to the pressure level exceeding a threshold level, and transferring, by at least the second pump, fluid from the fluid reservoir to the inflatable member during a second phase of the inflation cycle.

According to some aspects, the method may include one or more of the following features (or any combination thereof). The second pump may be disposed in parallel with the first pump during the first phase. The second pump may be disposed in parallel with the first pump during the second phase. The first pump and the second pump may be disposed in a parallel configuration during the first phase, and the method further includes switching to a serial configuration during the second phase. The serial configuration is a configuration in which the first pump is serially disposed with respect to the second pump.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to bodily implants. The term patient or user may hereafter be used for a person who benefits from the medical device or the methods disclosed in the present disclosure. For example, the patient can be a person whose body is implanted with the medical device or the method disclosed for operating the medical device by the present disclosure. For example, in some embodiments, the patient may be a human, or any other mammal.

Figure 1:
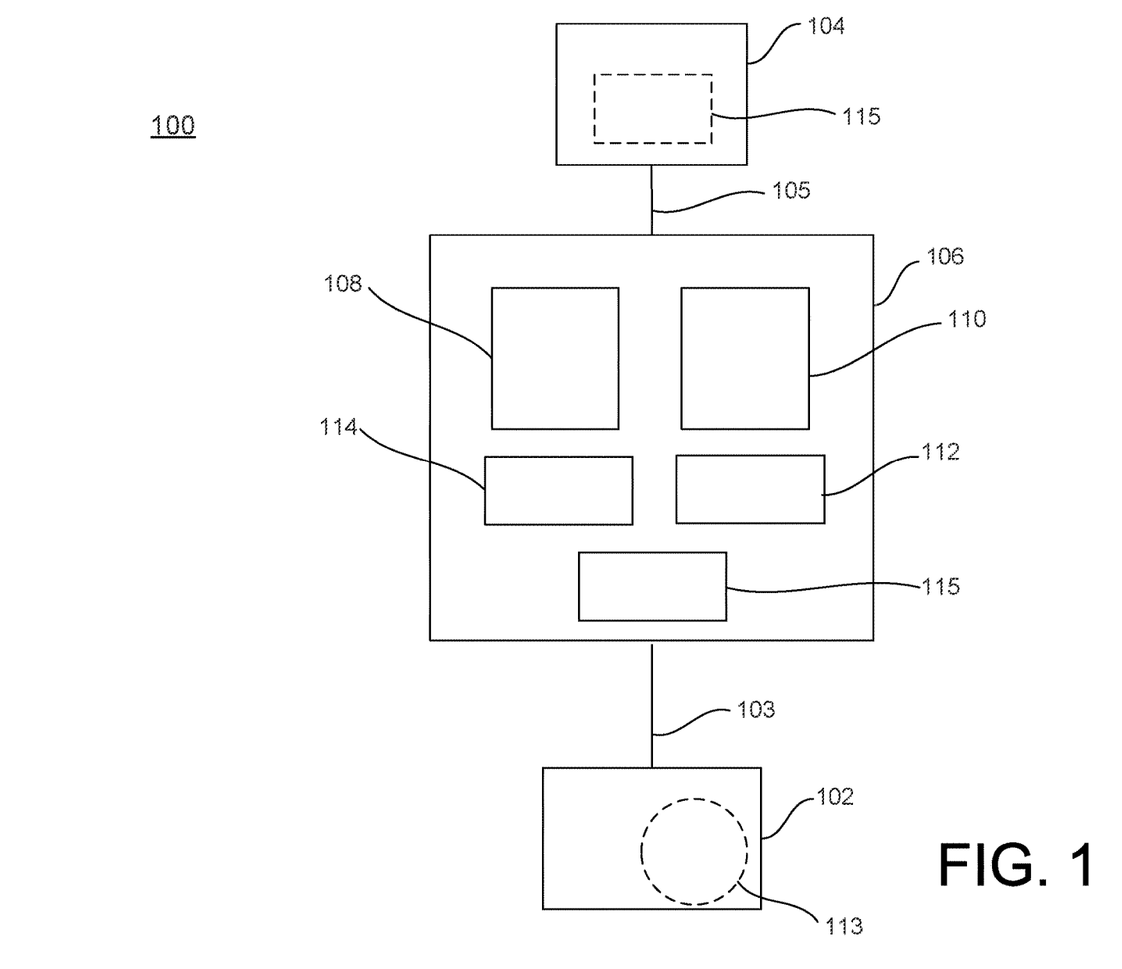
FIG. 1 illustrates an inflatable penile prosthesis having a pump assembly that includes a first pump and a second pump according to an aspect.

FIG. 1 illustrates an inflatable penile prosthesis 100 having a multiple pump system that can improve an inflation operation of the prosthesis's inflatable member according to an aspect. The inflatable penile prosthesis 100 may include a fluid reservoir 102, an inflatable member 104, and a pump assembly 106 configured to transfer fluid between the fluid reservoir 102 and the inflatable member 104. The inflatable member 104 may be implanted into the corpus cavernosae of the user, the fluid reservoir 102 may be implanted in the abdomen or pelvic cavity of the user (e.g., the fluid reservoir 102 may be implanted in the lower portion of the user's abdominal cavity or the upper portion of the user's pelvic cavity), and the pump assembly 106 may be implanted in the scrotum of the user.

The pump assembly 106 includes multiple pumps that pump fluid into the inflatable member 104 during an inflation cycle in a manner that increases the efficiency and/or decreases the amount of time required to fully inflate the inflatable member 104. In some examples, the multiple pumps operate at different time periods during the inflation cycle. In some examples, the multiple pumps operate at a same time during at least a portion of the inflation cycle. In some examples, the multiple pumps are not individually controlled by the user, but are mechanically and/or programmatically controlled by a controller 112, which from the point of view of the user, the multiple pumps of the pump assembly 106 may appear as a single pump. In some examples, the user is able to program the maximum output pressure and/or the pressure profile during intercourse. For example, the rigidity of the penile implant may be controlled such that preliminary ejaculation may be avoided.

The inflatable member 104 may be capable of expanding upon the injection of fluid into a cavity of the inflatable member 104. For instance, upon injection of the fluid into the inflatable member 104, the inflatable member 104 may increase its length and/or width, as well as increase its rigidity. In some examples, the inflatable member 104 may include a pair of inflatable cylinders or at least two cylinders, e.g., a first cylinder member and a second cylinder member. The volumetric capacity of the inflatable member 104 may depend on the size of the inflatable cylinders. In some examples, the volume of fluid in each cylinder may vary from about 10 milliliters in smaller cylinders and to about 50 milliliters in larger sizes. In some examples, the first cylinder member may be larger than the second cylinder member. In other examples, the first cylinder member may have the same size as the second cylinder member.

The fluid reservoir 102 may include a container having an internal chamber configured to hold or house fluid that is used to inflate the inflatable member 104. The volumetric capacity of the fluid reservoir 102 may vary depending on the size of the inflatable penile prosthesis 100. In some examples, the volumetric capacity of the fluid reservoir 102 may be 3 to 150 cubic centimeters. In some examples, the fluid reservoir 102 is constructed from the same material as the inflatable member 104. In other examples, the fluid reservoir 102 is constructed from a different material than the inflatable member 104. In some examples, the fluid reservoir 102 contains a larger volume of fluid than the inflatable member 104.

The inflatable penile prosthesis 100 may include a first conduit connector 103 and a second conduit connector 105. Each of the first conduit connector 103 and the second conduit connector 105 may define a lumen configured to transfer the fluid to and from the pump assembly 106. The first conduit connector 103 may be coupled to the pump assembly 106 and the fluid reservoir 102 such that fluid can be transferred between the pump assembly 106 and the fluid reservoir 102 via the first conduit connector 103. For example, the first conduit connector 103 may define a first lumen configured to transfer fluid between the pump assembly 106 and the fluid reservoir 102. The first conduit connector 103 may include a single or multiple tube members for transferring the fluid between the pump assembly 106 and the fluid reservoir 102.

The second conduit connector 105 may be coupled to the pump assembly 106 and the inflatable member 104 such that fluid can be transferred between the pump assembly 106 and the inflatable member 104 via the second conduit connector 105. For example, the second conduit connector 105 may define a second lumen configured to transfer fluid between the pump assembly 106 and the inflatable member 104. The second conduit connector 105 may include a single or multiple tube members for transferring the fluid between the pump assembly 106 and the inflatable member 104. In some examples, the first conduit connector 103 and the second conduit connector 105 may include a silicone rubber material. In some examples, the pump assembly 106 may be directly connected to the fluid reservoir 102.

The pump assembly 106 includes a first pump 108, a second pump 110, the controller 112, a sensor 115, and a power source 114. The pump assembly 106 may include other features such as a valve body, a pump bulb, one or more valves, and/or an inflation mode selector configured to select between an inflation mode and a deflation mode. In some examples, the pump assembly 106 includes more than two pumps such as three pumps or more than three pumps, which can be arranged in a parallel configuration and/or a serial configuration with respect to each (and may transition between the parallel configuration and the serial configuration during different phases of the inflation cycle).

The first pump 108 is configured to facilitate the transfer of fluid from the fluid reservoir 102 to the inflatable member 104 according to a first flow rate up to a first maximum output pressure. The second pump 110 is configured to facilitate transfer of fluid from the fluid reservoir 102 to the inflatable member 104 according to a second flow rate up to a second maximum output pressure. In some examples, the first flow rate is higher than the second flow rate. In some examples, the first maximum output pressure is lower than the second maximum output pressure. In some examples, the first pump 108 is a high capacity pump (e.g., high flow rate) but with relatively low output pressure. In some examples, the second pump 110 is a low capacity pump (e.g., low flow rate) but with relatively high output pressure.

Figure 2A:
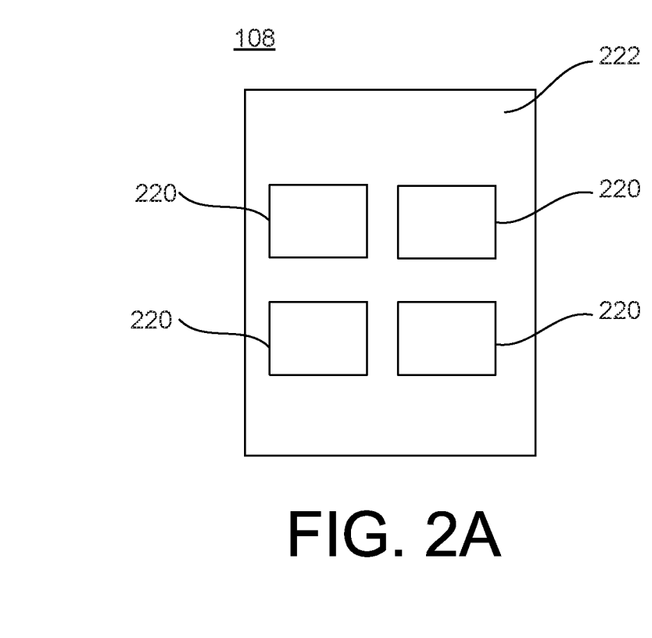
FIG. 2A illustrates an example of the first pump of the pump assembly according to an aspect.

The first pump 108 may include one or more devices configured to facilitate the transfer of fluid from the fluid reservoir 102 to the inflatable member 104. In some examples, referring to FIG. 2A, the first pump 108 includes micro-pumps 220 disposed on a first substrate 222, which are arranged to provide the first flow rate and the first maximum output pressure. In some examples, the micro-pumps 220 are piezoelectrically-driven micro-pumps. In some examples, the micro-pumps 220 include a first dimension in a range of 4 mm to 15 mm, a second dimension in a range of 4 mm to 15 mm, and/or a third dimension in a range of 0.4 mm to 2 mm. In some examples, the micro-pumps 220 include a silicon-based material. In some examples, the micro-pumps 220 includes a metal (e.g., steel) based material. In some examples, the first substrate 222 includes a wafer. Although FIG. 2A illustrates four micro-pumps 220, the embodiments encompass any number of micro-pumps 220 disposed on the first substrate 222 including one micro-pump or more than one micro-pump. In some examples, the first pump 108 includes more than ten micro-pumps 220 arranged on the first substrate 222. In some examples, the first pump 108 includes more than twenty micro-pumps 220 arranged on the first substrate 222. In some examples, the first pump 108 includes more than forty micro-pumps 220 arranged on the first substrate 222. In some examples, the micro-pumps 220 disposed on the first substrate 222 are non-mechanical (e.g., without moving parts).

The second pump 110 may include one or more devices configured to facilitate the transfer of fluid from the fluid reservoir 102 to the inflatable member 104. In some examples, referring to FIG. 2B, the second pump 110 includes micro-pumps 220 disposed on a second substrate 225, which are arranged to provide the second flow rate and the second maximum output pressure. In some examples, the first substrate 222 and the second substrate 225 are the same substrate (e.g., the micro-pumps 220 for the first pump 108 and the micro-pumps 220 for the second pump 210 are disposed on the same substrate). In some examples, the first substrate 222 and the second substrate 225 are different substrates.

Figure 2B:
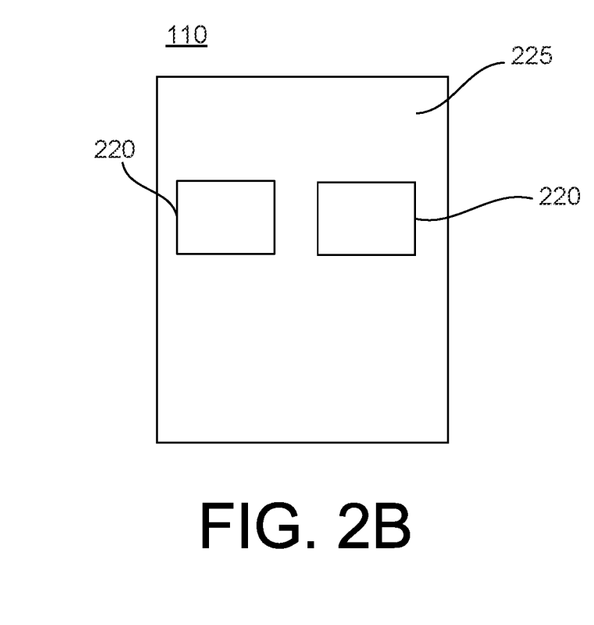
FIG. 2B illustrates an example of the second pump of the pump assembly according to an aspect.

In some examples, the second substrate 225 includes a wafer. Although FIG. 2B illustrates two micro-pumps 220 disposed on the second substrate 225, the embodiments encompass any number of micro-pumps 220 including one micro-pump or more than one micro-pump on the second substrate 225. In some examples, the second pump 110 includes more micro-pumps 220 than the first pump 108. In some examples, the second pump 110 includes less micro-pumps 220 than the first pump 108. In some examples, the second pump 110 includes two or more micro-pumps 220 arranged on the second substrate 225. In some examples, the second pump 110 includes more than ten micro-pumps 220 arranged on the second substrate 225. In some examples, the second pump 110 includes more than twenty micro-pumps 220 arranged on the second substrate 225. In some examples, the micro-pumps 220 disposed on the second substrate 225 are non-mechanical (e.g., without moving parts).

In some examples, the first pump 108 and the second pump 110 are arranged in a parallel configuration during an inflation cycle. In some examples, the first pump 108 and the second pump 110 are arranged in the parallel configuration during the entire inflation cycle. In some examples, the first pump 108 and the second pump 110 are arranged in the parallel configuration for only a portion of the inflation cycle. In the parallel configuration, each of the first pump 108 and the second pump 110 are configured to receive fluid from the fluid reservoir 102, and inject the fluid into the inflatable member 104 during the inflation cycle. In some examples, the first pump 108 is configured to fill the inflatable member 104 at the first flow rate up to the first maximum output pressure (e.g., higher flow rate, lower output pressure) during a first phase of the inflation cycle until the pressure level in the inflatable member 104 reaches a threshold level. In some examples, the threshold level is in relation to the total volume of the inflatable member 104. In some examples, the threshold level is in relation to the total amount of pressure in the inflatable member 104. Upon reaching the threshold level, the pump assembly 106 may activate (or switch to) to the second pump 110, and the second pump 110 injects the remaining amount of fluid at the second flow rate up to the second maximum output pressure (e.g., lower flow rate, higher output pressure). In some examples, the controller 112 may de-activate the first pump 108 during the second phase (e.g., after the second phase starts but before the second phase ends).

The sensor 115 is configured to monitor the pressure level in the inflatable member 104. In some examples, the sensor 115 is calibrated before the inflation and deflation cycle is commenced. The sensor 115 is communicatively coupled to the controller 112 such that the controller 112 can receive signals from the sensor 115. In some examples, the sensor 115 is included within the pump assembly 106. In some examples, the sensor 115 is configured to sense the amount of fluid transferred to the inflatable member 104, and send one or more signals to the controller 112 that indicate the amount of fluid that has been transferred.

In some examples, the sensor 115 is included within the inflatable member 104. In some examples, the sensor 115 is integrated in a wall of a cylinder of the inflatable member 104. In some example, when the sensor 115 is integrated in the wall of the cylinder, the sensor 115 may monitor the condition of the cylinder material, and the sensor 115 can monitor the changing of the cylinder material to a point where the cylinder might have to be replaced. In this case, the controller 112 may send information, over a network, to an external device (e.g., located at a hospital or doctor's office) on a regular basis for potential checkups.

In some examples, the sensor 115 is configured to sense the pressure level in the inflatable member 104 and send one or more signals to the controller 112 that indicate the pressure level in the inflatable member 104. In some examples, the sensor 115 is configured to monitor the flowrate (e.g., the flowrate in both directions). The controller 112 may control the activation (and deactivation) of the first pump 108 and the second pump 110 based on the signals received from the sensor 115 such that the operator is unaware of that the pump assembly 106 includes multiple pumps operating at different times. In some examples, the controller 112 may send activation signals or deactivation signals to the first pump 108 and the second pump 110 to controls the activation and deactivation of the first pump 108 and the second pump 110.

During the first phase of the inflation cycle, the controller 112 may activate the first pump 108 and deactivate the second pump 110 such that the fluid is injected into the inflatable member 104 using the first pump 108. The controller 112 may monitor the pressure level in the inflatable member 104, and/or the amount of fluid that is transferred by the pump assembly 106 (or contained in the inflatable member 104) (e.g., based on the signals received from the sensor 115), and when the level meets or exceeds the threshold level, the controller 112 may deactivate the first pump 108 and activate the second pump 110 such that the second pump 110 can fill the remaining amount of the inflatable member 104. In some examples, the threshold level is an amount within the range of 85% to 95% of the total volume of the inflatable member 104. In some examples, the threshold level is substantially 90% of the total volume of the inflatable member 104. In some examples, the controller 112 may monitor the pressure in the inflatable member 104, and when the pressure meets or exceeds the threshold level, the controller 112 may deactivate the first pump 108 and activate the second pump 110 such that the second pump 110 can fill the remaining amount of the inflatable member 104. In some examples, the threshold level is at 80% to 90% of the maximum operating pressure level of a fully inflated inflatable member 104.

The power source 114 is configured to provide a power source for the controller 112. In some examples, the controller 112 includes at least one processor (e.g., coupled to a substrate) and a non-transitory computer-readable medium storing executable code, that when executed by the at least one processor, is configured to perform the operations of the controller 112 discussed herein. In some examples, the power source 114 includes a battery. In some examples, the controller 112 may include one or more moving parts in order to control open and close valves associated with the pump assembly 106.

In some examples, the controller 112 is configured to control one or more valves to transition the first pump 108 and the second pump 110 between a parallel configuration and a serial configuration during different phases of the inflation cycle. The valves may be disposed in fluid passageways within a valve body or block of the pump assembly 106. In some examples, during the first phase of the inflation cycle, the first pump 108 and the second pump 110 are arranged in the parallel configuration. In some examples, the controller 112 is configured to actuate one or more valves (e.g., place the valves in either an open position where fluid can flow through a valve or a closed position in which fluid is blocked) to arrange the first pump 108 and the second pump 110 in the parallel configuration. In some examples, during the first phase of the inflation cycle, both the first pump 108 and the second pump 110 are activated to transfer fluid from the fluid reservoir 102 to the inflatable member 104. In some examples, only the first pump 108 is activated to transfer fluid to the inflatable member 104.

In some examples, the first pump 108 is activated to fill the inflatable member 104 at the first flow rate up to the first maximum output pressure until the inflatable member 104 exceeds the threshold level (e.g., a fluid amount detected, or pressure level, or strain of the inflatable member, by the controller 112 exceeding the threshold level). Upon the detection of exceeding the threshold level by the controller 112, the controller 112 is configured to actuate one or more valves to arrange the first pump 108 and the second pump 110 in the serial configuration. Then, the first pump 108 and the second pump 110 (in series with one another) are configured to fill the remaining amount of the inflatable member 104 during the second phase of the inflation cycle. In some examples, in the serial configuration, the first pump 108 is disposed before the second pump 110 such that the second pump 110 receives the output of the first pump 108 and the output of the second pump 110 is transferred to the inflatable member 104. In other examples, in the serial configuration, the second pump 110 is disposed before the first pump 108 such that the first pump 108 receives the output of the second pump 110, and the output of the second pump 110 is transferred to the inflatable member 104.

In some examples, the fluid reservoir 102 includes a flexible fluid container 113. For example, the flexible fluid container 113 may be a structure separate from the fluid reservoir 102 but disposed inside the cavity of the fluid reservoir 102. In some examples, the flexible fluid container 113 includes an expandable balloon disposed inside the cavity of the fluid reservoir 102. In some examples, during a preliminary period (e.g., before the start of the inflation cycle), the pump assembly 106 may displace fluid from the fluid reservoir 102 into the flexible fluid container 113 causing the flexible fluid container 113 to expand and increase the pressure inside the flexible fluid container 113.

In some examples, the controller 112 is configured to activate one or more valves to direct a fluid flow from the fluid reservoir 102 to the flexible fluid container 113, and the fluid is pumped into the flexible fluid container 113 using the first pump 108 and/or the second pump 110. In some examples, the controller 112 may activate the second pump 110 to transfer the fluid from the fluid reservoir 102 into the flexible fluid container 113. The transfer of the fluid into the flexible fluid container 113 may temporarily store energy into the wall of the flexible fluid container 113 which can be used later to inflate the inflatable member at high pressure. The energy is stored through the elastic expansion of the wall of the flexible fluid container 113.

In some examples, during a first phase of the inflation cycle, the first pump 108 (and/or the second pump 110) is/are activated to transfer the fluid from the fluid reservoir 102 to the inflatable member 104 until reaching the threshold level. Then, during a second phase of the inflation cycle, the controller 112 may actuate the valves to define a fluid passageway within the pump assembly 106 between the flexible fluid container 113 and the inflatable member 104 such that the remaining amount is transferred from the flexible fluid container 113 to the inflatable member 104 at a relatively high output pressure. For example, upon defining (or opening) the fluid passageway between the flexible fluid container 113 and the inflatable member 104, the fluid automatically flows from the high pressure of the flexible fluid container 113 to the lower pressure of the inflatable member 104. After transferring fluid from the flexible container to the inflatable member 104, the controller 112 may close the fluid connection between them by closing the valve.

In some examples, the flexible fluid container 113 is used to transfer fluid to the inflatable member at a higher output pressure at a particular point or phase in the use of the inflatable member 104 (e.g., at a point in time after the inflation cycle). For example, the controller 112 may include a sensor configured to sense a point in time during or before the ejaculation period of the user of the inflatable penile prosthesis 100, and upon sensing that point, the controller 112 may actuate one or more valves to establish the fluid passageway from the flexible fluid container 113 to the inflatable member 104 (which results in the transfer of fluid from the flexible fluid container 113 to the inflatable member 104) such that the pressure in the inflatable member 104 increases during the ejaculation period. In some examples, the sensor may detect the blood pressure, the heart rate, or the breathing rate of the user.

Figure 3:
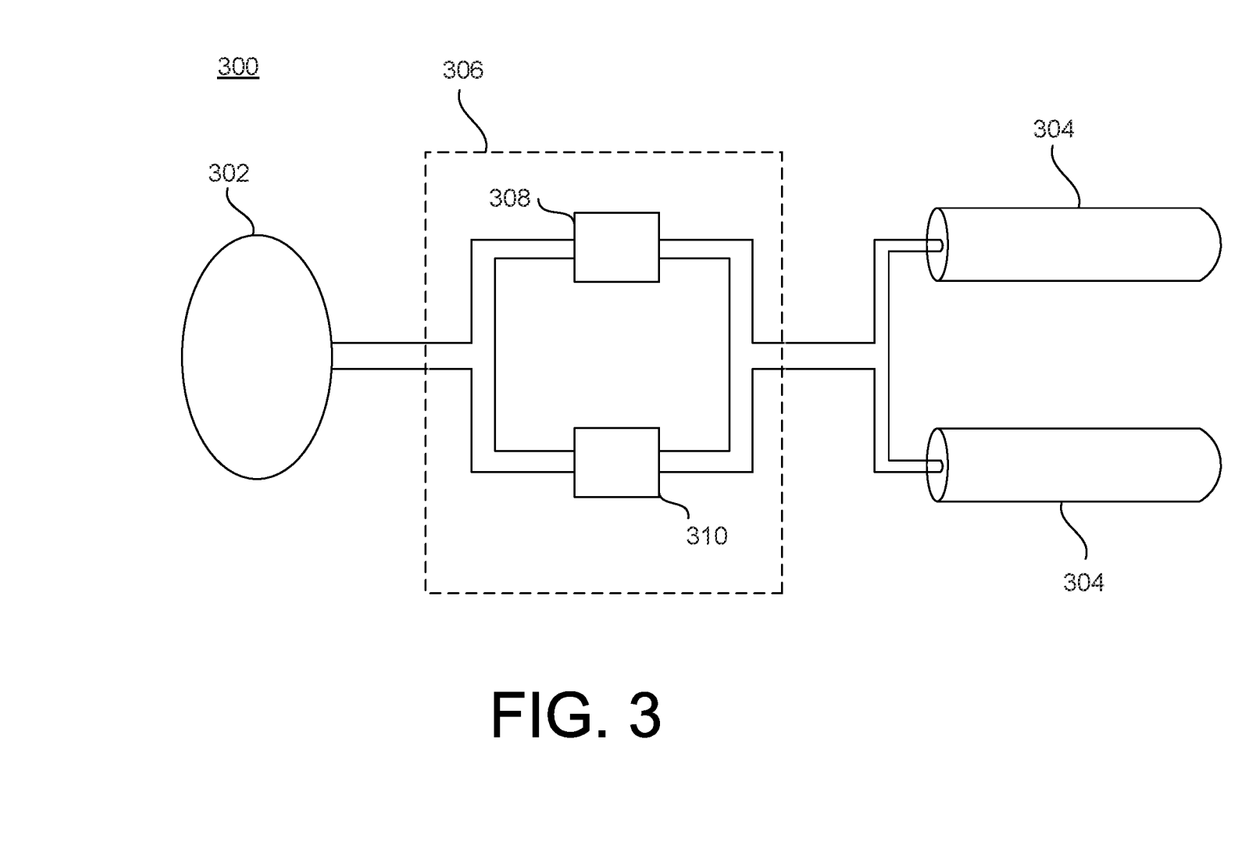
FIG. 3 illustrates an inflatable penile prosthesis having a pump assembly that includes a first pump in parallel with a second pump according to an aspect.

FIG. 3 illustrates an inflatable penile prosthesis 300 including a pump assembly 306 that has a first pump 308 and a second pump 310 in a parallel configuration according to an aspect. The pump assembly 306 is configured to transfer fluid from a fluid reservoir 302 to a pair of inflatable cylinders 304 during an inflation cycle. The first pump 308 is disposed in parallel with the second pump 310. The fluid reservoir 302 may include any of the features described with reference to the fluid reservoir 102 of FIG. 1. The inflatable cylinders 304 may include any of the features described with reference to the inflatable member 104 of FIG. 1. The pump assembly 306 may include any of the features discussed with reference to FIGS. 1, 2A, and 2B.

The pump assembly 306 may define fluid passageways that arrange the first pump 308 and the second pump 310 in parallel with respect to each other. An input of the first pump 308 is fluidly coupled to the fluid reservoir 302, and an output of the first pump 308 is fluidly coupled to the inflatable cylinders 304. An output of the second pump 310 is fluidly coupled to the fluid reservoir 302, and an output of the first pump 308 is fluidly coupled to the inflatable cylinders 304.

In some examples, the first pump 308 is configured to inject fluid into the inflatable cylinders 304 during a first phase of an inflation cycle, and the second pump 310 is configured to inject fluid into the inflatable cylinders 304 during a second phase of the inflation cycle, where the second phase is after the first phase. In other examples, the first pump 308 and the second pump 310 are configured to simultaneously inject fluid into the inflatable cylinders 304 during the inflation cycle. In some examples, the first pump 308 is configured to fill the inflatable cylinders 304 at a first flow rate up to a first maximum output pressure (e.g., higher flow rate, lower output pressure) during the first phase until the inflatable cylinders 304 reach the threshold level. Upon reaching the threshold level, the pump assembly 306 may activate the second pump 310 and inject the remaining amount at the lower flow rate but higher output pressure.

In some examples, the pump assembly 306 includes a controller (e.g., the controller 112 of FIG. 1) and a sensor (e.g., the sensor 115 of FIG. 1). The controller is configured to monitor the pressure level and/or the amount of fluid transferred to the inflatable cylinders 304 (e.g., based on the signals received from the sensor), and control the activation and deactivation of the first pump 308 and the second pump 310 such that the operator is unaware of that the pump assembly 306 includes multiple pumps. At the start of the inflation cycle, in some examples, the controller may activate the first pump 308 and deactivate the second pump 310 such that the fluid is injected into the inflatable cylinders 304 using the first pump 308 during the first phase. In response to the fluid or pressure level meeting or exceeding the threshold level, the controller may deactivate the first pump 308 and activate the second pump 310 so that the second pump 310 can fill the remaining amount of the inflatable cylinders 304. In some examples, the threshold level is an amount within the range of 85% to 95% of the total volume of the inflatable cylinders 304. In some examples, the threshold level is substantially 90% of the total volume of the inflatable cylinders 304. In some examples, the threshold level is at 80% to 90% of the maximum operating pressure level of a fully inflated inflatable member 104.

FIGS. 4A through 4E illustrate an inflatable penile prosthesis 400 including a pump assembly 406 that has a first pump 408 and a second pump 410 configured to transition between a parallel configuration and a serial configuration according to an aspect. The pump assembly 406 is configured to transfer fluid from a fluid reservoir 402 to a pair of inflatable cylinders 404 during an inflation cycle. The fluid reservoir 402 may include any of the features described with reference to the fluid reservoir 102 of FIG. 1. The inflatable cylinders 404 may include any of the features described with reference to the inflatable member 104 of FIG. 1. The pump assembly 406 may include any of the features of the pump assembly (e.g., 106, 306) discussed with reference to FIGS. 1, 2A, and 2B.

The pump assembly 406 includes a plurality of valves such as a valve 430, a valve 432, and a valve 434, which are disposed within fluid passageways of the valve block or body of the pump assembly 406. Each of the valve 430, the valve 432, and the valve 434 may include a device for controlling the passage of fluid through the fluid passageway in which it is disposed. Each of the valve 430, the valve 432, and the valve 434 includes an open position in which fluid is permitted to travel through the passageway, and a closed position in which fluid is not permitted to travel through the passageway. Although FIGS. 4A-4E graphically represent the valves as switches, the open position of the valve indicates that fluid may pass through the valve, and the closed position of the valve indicates that fluid may be prevented from passing through the valve. Also, the pump assembly 406 includes a controller (e.g., the controller 112 of FIG. 1) configured to control the actuation (e.g., the opening and closing) of the valve 430, the valve 432, and the valve 434. Each of the valve 430, the valve 432, and the valve 434 includes a first port and a second port. In the closed position, fluid does not transfer between the first port and the second port. In the open position, fluid is permitted to transfer between the first port and the second.

An input of the first pump 408 may be fluidly coupled to the fluid reservoir 402, and an input of the second pump 410 may be selectively coupled to the fluid reservoir 402 (via the valve 430). An output of the first pump 408 is selectively coupled to the inflatable cylinders 404 (via the valve 434), and the output of the first pump 408 is selectively coupled to the input of the second pump 410 (via the valve 432). The output of the second pump 410 is fluidly coupled to the inflatable cylinders 404.

Figure 4A:
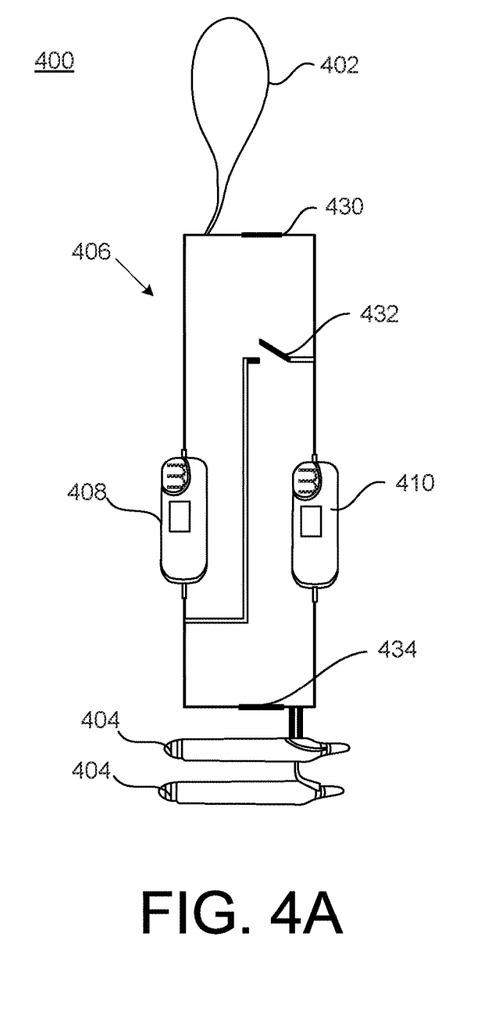
FIG. 4A illustrates an inflatable penile prosthesis having a multiple pump assembly in a first configuration according to an aspect.

As shown in FIG. 4A, during a first phase of an inflation cycle, the first pump 408 and the second pump 410 are arranged in the parallel configuration. In the parallel configuration, the valve 430 is in the open position, the valve 432 is in the closed position, and the valve 434 is in the open position. In the parallel configuration, the first pump 408 is disposed in parallel with respect to the second pump 410. In some examples, the first pump 408 is configured to inject fluid from the fluid reservoir 402 to the inflatable cylinders 404 during the first phase of the inflation cycle. In some examples, the first pump 408 and the second pump 410 are configured to inject fluid from the fluid reservoir 402 to the inflatable cylinders 404 during the first phase of the inflation cycle.

Figure 4B:
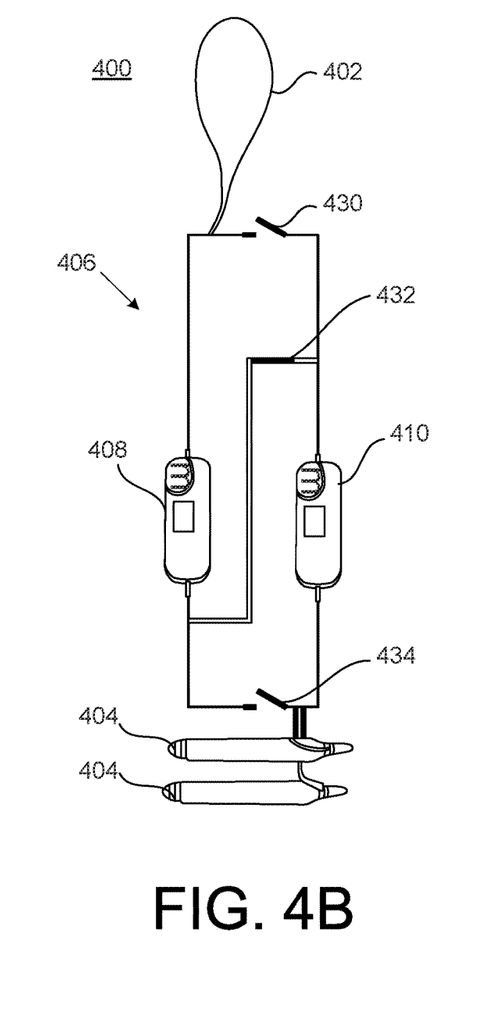
FIG. 4B illustrates the inflatable penile prosthesis having the multiple pump assembly in a second configuration according to an aspect.

As shown in FIG. 4B, during a second phase of the inflation cycle, the first pump 408 and the second pump 410 are arranged in the series configuration. In some examples, the controller is configured to control valve 430, the valve 432, and the valve 434 to arrange the first pump 408 and the second pump 410 in the series configuration. In some examples, in the series configuration, the valve 430 is in the closed position, the valve 432 is in the open position, and the valve 434 is in the closed position. In some examples, during the second phase, the first pump 408 is connected to and receives the fluid from the fluid reservoir 402, and the output of the second pump 410 is connected to the input of the second pump 410. The first pump 408 and the second pump 410 are configured to serially pump the fluid from the fluid reservoir 402 to the inflatable cylinders 404.

Figure 4C:
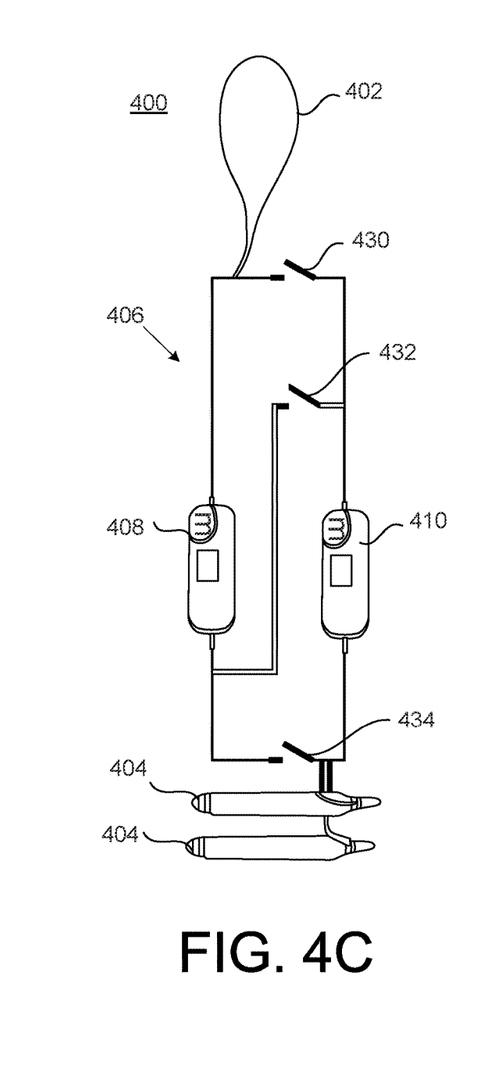
FIG. 4C illustrates the inflatable penile prosthesis having the multiple pump assembly in a third configuration according to an aspect.
Figure 4D:
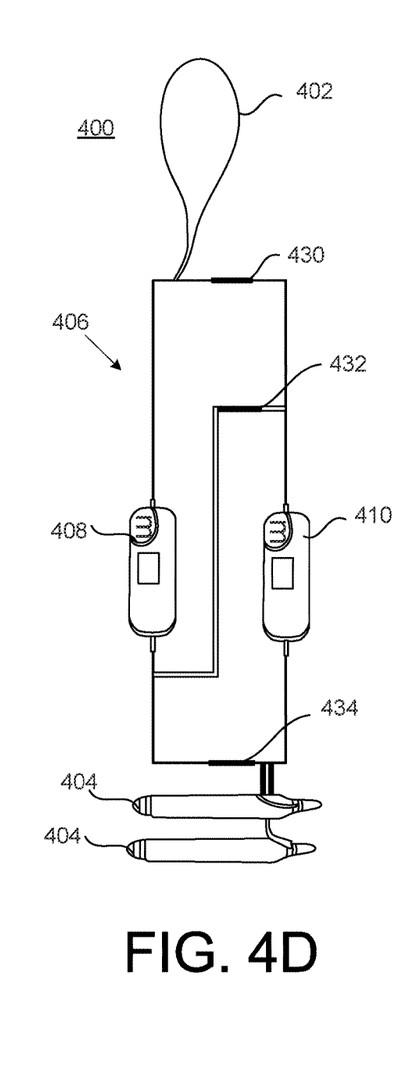
FIG. 4D illustrates the inflatable penile prosthesis having the multiple pump assembly in a fourth configuration according to an aspect.
Figure 4E:
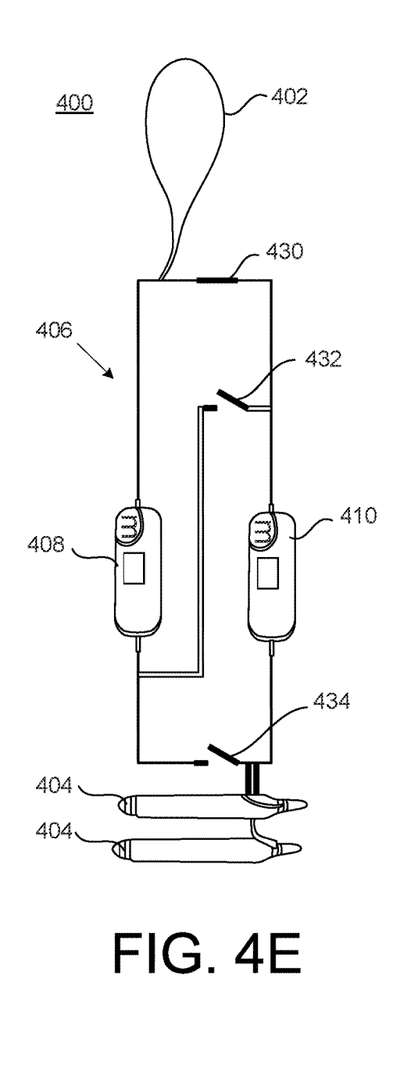
FIG. 4E illustrates the inflatable penile prosthesis having the multiple pump assembly in a fifth configuration according to an aspect.

As shown in FIG. 4C, during a third phase (e.g., the hold phase) of the inflation cycle, the valve 430 is in the closed position, the valve 432 is in the closed position, and the valve 434 is in the closed position, thereby disconnecting the fluid reservoir 402 from the inflatable cylinders 404. As shown in FIG. 4D, during a fourth phase (e.g., release phase), the valve 430 is in the open position, the valve 432 is in the open position, and the valve 434 is in the open position. As shown in FIG. 4E, during a fifth phase (e.g., normal operation), the valve 430 is in the open position, the valve 432 is in the closed position, and the valve 434 is in the closed position.

Figure 5A:
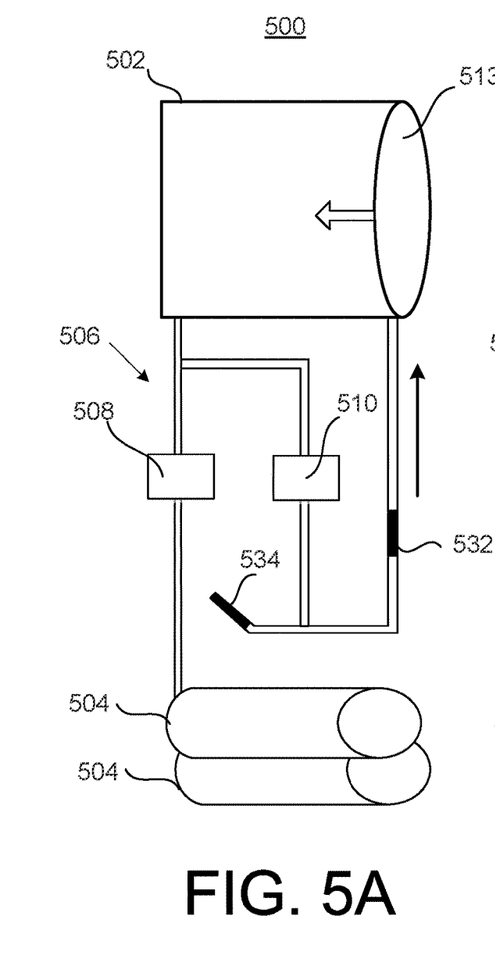
FIG. 5A illustrates an inflatable penile prosthesis having a pump assembly and a flexible fluid container in a first configuration according to an aspect.
Figure 5B:
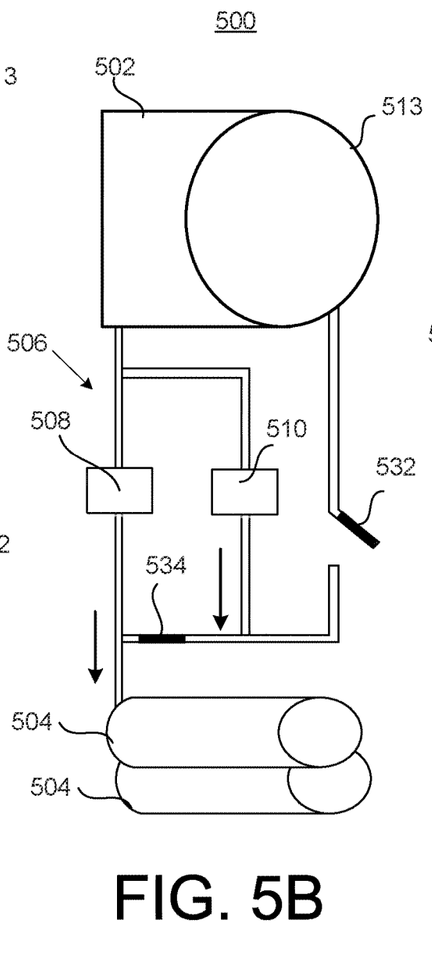
FIG. 5B illustrates the inflatable penile prosthesis having the pump assembly and the flexible fluid container in a second configuration according to an aspect.
Figure 5C:
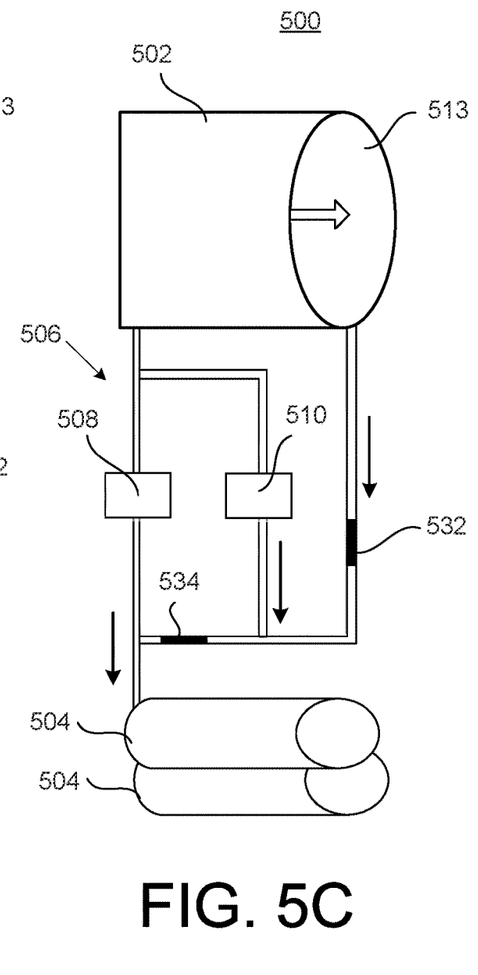
FIG. 5C illustrates the inflatable penile prosthesis having the pump assembly and the flexible fluid container in a third configuration according to an aspect.

FIGS. 5A through 5C illustrate an inflatable penile prosthesis 500 according to another aspect. The inflatable penile prosthesis 500 includes a pair of inflatable cylinders 504, a flexible fluid container 513 disposed inside of a fluid reservoir 502, and a pump assembly 506 configured to transfer fluid from the fluid reservoir 502 to the inflatable cylinders 504 during an inflation cycle. The pump assembly 506 may include a first pump 508, a second pump 510, a valve 532, and a valve 534. The fluid reservoir 502 may include any of the features described with reference to the fluid reservoir 102 of FIG. 1. The inflatable cylinders 504 may include any of the features described with reference to the inflatable member 104 of FIG. 1. The pump assembly 506 may include any of the features of the pump assembly discussed with reference to FIGS. 1, 2A, 2B, and 4. For example, the pump assembly 506 may include a controller (e.g., the controller 112) that controls the activation or deactivation of the first pump 508 and the second pump 510, and controls the actuating (e.g., the opening and closing) of the valve 532 and the valve 534.

In some examples, the flexible fluid container 513 may be pressurized during a preliminary phase before the inflation cycle. The flexible fluid container 513 may include a flexible balloon disposed inside of the cavity of the fluid reservoir 502. In response to the injection of fluid within the cavity of the flexible fluid container 513, the flexible fluid container 513 may expand causing the pressure to increase inside of the flexible fluid container 513. As shown in FIG. 5A, during the preliminary phase, the valve 534 is in the closed position, and the valve 532 is in the open position. During the preliminary phase, the second pump 510 may transfer fluid from the fluid reservoir 502 to the flexible fluid container 513, which causes the flexible fluid container 513 to expand.

Referring to FIG. 5B, in a first phase of the inflation cycle, the controller may move the valve 534 from the closed position to the open position, and move the valve 532 from the open position to the closed position. In the first phase of the inflation cycle, the first pump 508 and/or the second pump 510 may transfer fluid from the fluid reservoir 502 to the inflatable cylinders 504. Referring to FIG. 5C, in a second phase (e.g., the last part and/or the high pressure part) of the inflation cycle, the controller may cause the valve 532 to transition to the open position, and the valve 534 remains in the open position. In the second phase, when the valve 532 transitions to the open position, fluid from the flexible fluid container 513 is transferred to the inflatable cylinders 504 causing the flexible fluid container 513 to contract.

Figure 6:
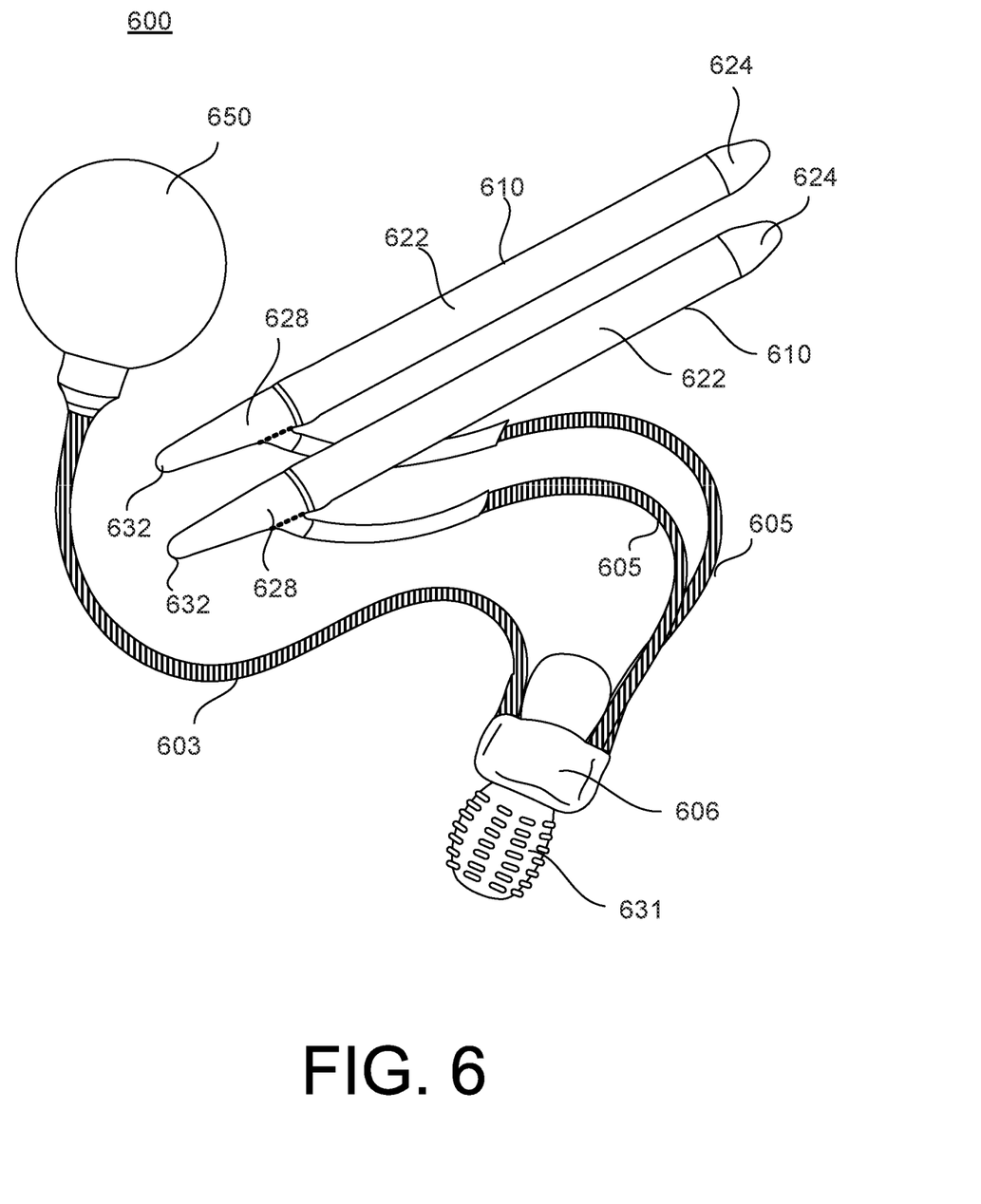
FIG. 6 illustrates an inflatable penile prosthesis having the multiple pump assembly according to an aspect.

FIG. 6 schematically illustrates an inflatable penile prosthesis 600 having a pump assembly 606 according to an aspect. The pump assembly 606 may include any of the features of the pump assembly (e.g., 106, 306, 406, 506) described with reference to the previous figures. The penile prosthesis 600 may include a pair of inflatable cylinders 610, and the inflatable cylinders 610 are configured to be implanted in a penis. For example, one of the inflatable cylinders 610 may be disposed on one side of the penis, and the other inflatable cylinder 610 may be disposed on the other side of the penis. Each inflatable cylinder 610 may include a first end portion 624, a cavity or inflation chamber 622, and a second end portion 628 having a rear tip 632.

The pump assembly 606 may be implanted into the patient's scrotum. A pair of conduit connectors 605 may attach the pump assembly 606 to the inflatable cylinders 610 such that the pump assembly 606 is in fluid communication with the inflatable cylinders 610. Also, the pump assembly 606 may be in fluid communication with a fluid reservoir 650 via a conduit connector 603. The fluid reservoir 650 may be implanted into the user's abdomen. The inflation chamber or portion 622 of the inflatable cylinder 610 may be disposed within the penis. The first end portion 624 of the inflatable cylinder 610 may be at least partially disposed within the crown portion of the penis. The second end portion 628 may be implanted into the patient's pubic region PR with the rear tip 632 proximate the pubic bone PB.

In order to implant the inflatable cylinders 610, the surgeon first prepares the patient. The surgeon often makes an incision in the penoscrotal region, e.g., where the base of the penis meets with the top of the scrotum. From the penoscrotal incision, the surgeon may dilate the patient's corpus cavernosae to prepare the patient to receive the inflatable cylinders 610. The corpus cavernosum is one of two parallel columns of erectile tissue forming the dorsal part of the body of the penis, e.g., two slender columns that extend substantially the length of the penis. The surgeon will also dilate two regions of the pubic area to prepare the patient to receive the second end portion 628. The surgeon may measure the length of the corpora cavernosae from the incision and the dilated region of the pubic area to determine an appropriate size of the inflatable cylinders 610 to implant.

After the patient is prepared, the penile prosthesis 600 is implanted into the patient. The tip of the first end portion 624 of each inflatable cylinder 610 may be attached to a suture. The other end of the suture may be attached to a needle member (e.g., Keith needle). The needle member is inserted into the incision and into the dilated corpus cavernosum. The needle member is then forced through the crown of the penis. The surgeon tugs on the suture to pull the inflatable cylinder 610 into the corpus cavernosum. This is done for each inflatable cylinder 610 of the pair. Once the inflation chamber 622 is in place, the surgeon may remove the suture from the tip. The surgeon then inserts the second end portion 628. The surgeon inserts the rear end of the inflatable cylinder 610 into the incision and forces the second end portion 628 toward the pubic bone PB until each inflatable cylinder 610 is in place.

A pump bulb 631 of the pump assembly 606 may be squeezed or depressed by the user in order to facilitate the transfer of fluid from the fluid reservoir 650 to the inflatable cylinders 610. For example, in the inflation mode, while the user is operating the pump bulb 631, the pump bulb 631 may receive the fluid from the fluid reservoir 650, and then output the fluid to the inflatable cylinders 610. When the user switches to the deflation mode, at least some of the fluid can automatically be transferred back to the fluid reservoir 650 (due to the difference in pressure from the inflatable cylinders 610 to the fluid reservoir 650). Then, the user may squeeze the inflatable cylinders 610 to facilitate the further transfer of fluid through the pump bulb 631 to the fluid reservoir 650.

Figure 7:
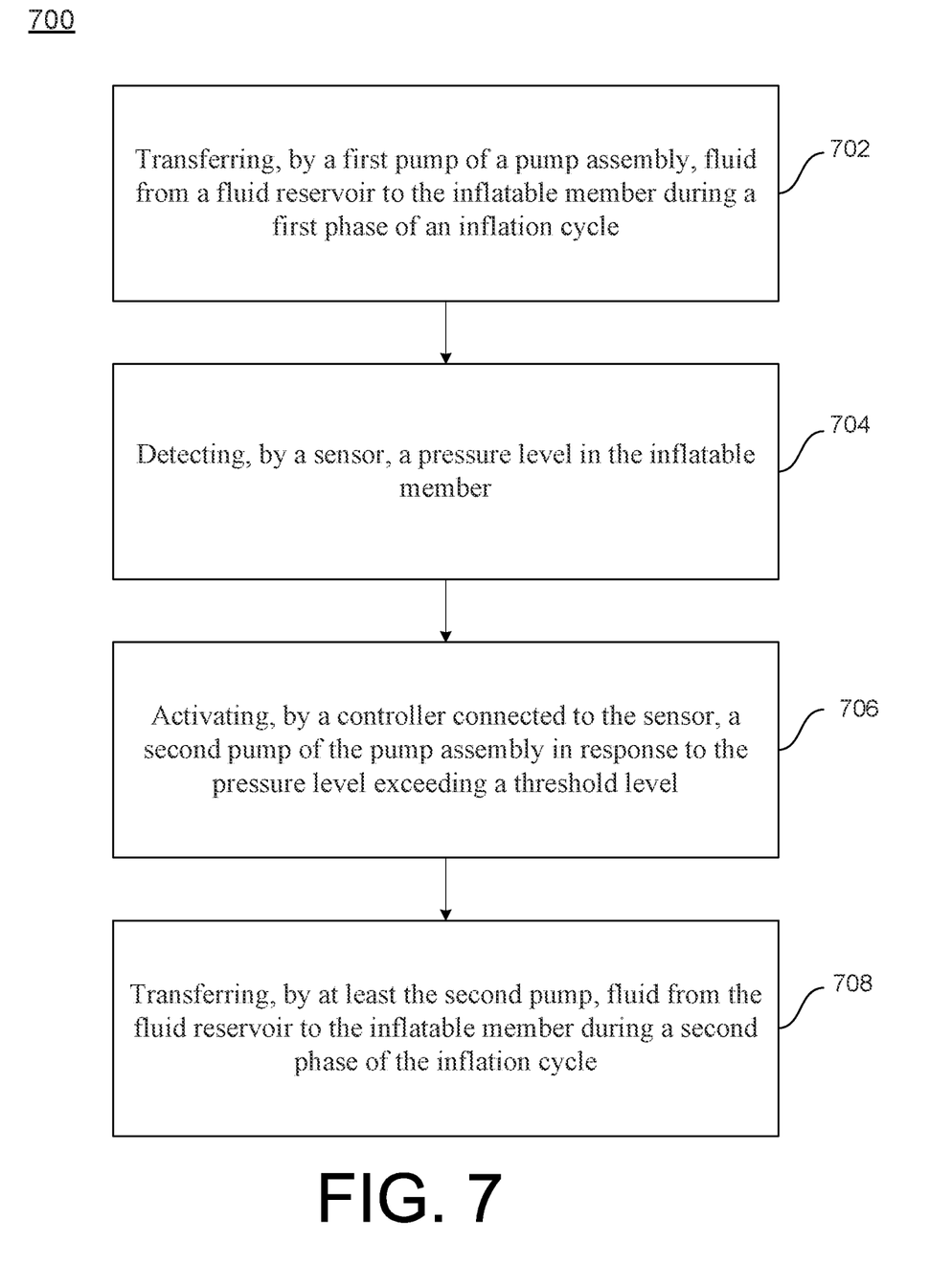
FIG. 7 illustrates a flow chart depicting example operations of a pump assembly according to an aspect.

FIG. 7 illustrates a flow chart 700 depicting example operations of a method of inflating an inflatable member of a penile prosthesis. The example operations of the flow chart 700 may be performed by any of the pump assemblies (e.g., 106, 306, 406, 506, 606) discussed herein.

Operation 702 includes transferring, by a first pump of a pump assembly, fluid from a fluid reservoir to the inflatable member during a first phase of an inflation cycle. Operation 704 includes detecting, by a sensor, a pressure level in the inflatable member. Operation 706 includes activating, by the controller, a second pump of the pump assembly in response to the pressure level exceeding a threshold level. Operation 708 includes transferring, by at least the second pump, fluid from the fluid reservoir to the inflatable member during a second phase of the inflation cycle.

In some examples, the second pump is disposed in parallel with the first pump during the first phase. In some examples, the second pump is disposed in parallel with the first pump during the second phase. In some examples, the first pump and the second pump are disposed in a parallel configuration during the first phase, where the method further includes switching to a serial configuration during the second phase. The serial configuration is a configuration in which the first pump is serially disposed with respect to the second pump.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. An apparatus, comprising:
a fluid reservoir configured to hold fluid;
an inflatable member; and
a pump assembly configured to transfer the fluid from the fluid reservoir to the inflatable member during an inflation cycle, the pump assembly including:
a first pump configured to inject the fluid into the inflatable member; and
a second pump configured to inject the fluid into the inflatable member,
wherein the pump assembly is configured to be disposed in a first configuration in which the second pump is disposed in parallel with the first pump and a second configuration in which the second pump is disposed in serial with the first pump.

2. The apparatus of claim 1, wherein the first pump includes a plurality of micro-pumps, and the second pump includes a plurality of micro-pumps.

3. The apparatus of claim 1, wherein the first pump is configured to inject the fluid into the inflatable member up to a first maximum output pressure, and the second pump is configured to inject the fluid into the inflatable member up to a second maximum output pressure, the second maximum output pressure being higher than the first maximum output pressure.

4. The apparatus of claim 1, wherein the second pump is disposed in parallel with the first pump.

5. The apparatus of claim 1, wherein the fluid reservoir includes a flexible fluid container disposed within a cavity of the fluid reservoir, the flexible fluid container enclosing fluid at a higher pressure than the fluid contained in the fluid reservoir.

6. The apparatus of claim 5, wherein at least one of the first pump or the second pump is configured to transfer the fluid in the fluid reservoir during a first phase of the inflation cycle, the fluid contained in the flexible fluid container being transferred to the inflatable member during a second phase of the inflation cycle.

7. The apparatus of claim 1, further comprising:
a controller configured to activate the first pump during a first phase of the inflation cycle,
the controller configured to activate the second pump during a second phase of the inflation cycle.

8. The apparatus of claim 7, wherein the controller is configured to activate the second pump during the second phase of the inflation cycle in response to a pressure level in the inflatable member exceeding a threshold level.

9. The apparatus of claim 1, further comprising:
a controller configured to actuate a plurality of valves to move between the parallel configuration and the serial configuration.

10. An apparatus, comprising:
a fluid reservoir configured to hold fluid;

an inflatable member; and
a pump assembly configured to transfer the fluid from the fluid reservoir to the inflatable member during an inflation cycle, the pump assembly including:
- a first pump configured to inject the fluid into the inflatable member, the first pump includes a plurality of micro-pumps;
- a second pump configured to inject the fluid into the inflatable member; and
- a controller configured to activate the first pump and the second pump.

11. The apparatus, of claim 10, wherein the plurality of micro-pumps of the first pump are disposed on a first substrate, and the second pump includes a plurality of micro-pumps disposed on a second substrate.

12. The apparatus, of claim 11, wherein a number of the plurality of micro-pumps disposed on the first substrate is less than a number of the plurality of micro-pumps disposed on the second substrate.

13. The apparatus, of claim 10, wherein the first pump is configured to inject the fluid into the inflatable member according to a first flow rate up to a first maximum output pressure, and the second pump is configured to inject the fluid into the inflatable member according to a second flow rate up to a second maximum output pressure, the first flow rate being higher than the second flow rate, the second maximum output pressure being higher than the first maximum output pressure.

14. The apparatus of claim 10, wherein the fluid reservoir includes a flexible fluid container disposed within a cavity of the fluid reservoir, the flexible fluid container configured to enclose the fluid at a higher pressure than the fluid contained in the fluid reservoir.

15. A method, comprising:
transferring, by a first pump of a pump assembly, an amount of fluid from a fluid reservoir to the inflatable member during a first phase of an inflation cycle, the first pump and a second pump of the pump assembly being disposed in a parallel configuration during the first phase of the inflation cycle;
switching to a serial configuration, the serial configuration being a configuration in which the first pump is disposed in a series with the second pump; and
transferring, by at least the second pump, an amount of fluid from the fluid reservoir to the inflatable member during a second phase of the inflation cycle.

16. The method of claim 15, further comprising:
detecting, by a sensor, a pressure level in the inflatable member.

17. The method of claim 15, further comprising:
detecting, by a sensor, a pressure level in the inflatable member; and
activating, by a controller connected to the sensor, the second pump of the pump assembly in response to the pressure level exceeding a threshold level.

* * * * *